United States Patent [19]
Takeuchi et al.

[11] Patent Number: 5,661,027
[45] Date of Patent: Aug. 26, 1997

[54] GEOTHERMAL POWER PLANT DESULFURIZATION METHOD

[75] Inventors: Kazuhisa Takeuchi; Yuuichi Fujioka, both of Nagasaki, Japan

[73] Assignee: Mitsubishi Jukogyo Kabushiki Kaisha, Tokyo, Japan

[21] Appl. No.: 503,642

[22] Filed: Jul. 18, 1995

[30] Foreign Application Priority Data

Aug. 24, 1994 [JP] Japan .................................. 6-199473
Nov. 8, 1994 [JP] Japan .................................. 6-273400
Dec. 20, 1994 [JP] Japan .................................. 6-316471

[51] Int. Cl.$^6$ .................................................. C12S 1/00
[52] U.S. Cl. .................................................. 435/266; 546/282
[58] Field of Search .................................. 435/262, 262.5, 435/266, 281, 282, 130, 41; 60/641.2, 641.6, 643, 645; 423/511, 576.2, DIG. 19

[56] References Cited

U.S. PATENT DOCUMENTS 4,760,027 7/1988 Sublette ..................... 435/266
5,387,523 2/1995 Monticello ..................... 435/282

Primary Examiner—George Yeung
Attorney, Agent, or Firm—Wenderoth, Lind & Ponack

[57] ABSTRACT

In a method of desulfurization used at a geothermal power plant, stem removed from a production well, after being used for power generation, is condensed and separated into condensed water and hydrogen sulfide-containing gas, and the hydrogen sulfide-containing gas is treated at biochemical treatment tank. The initial cell density of the reactor liquid of the biochemical treatment tanks is adjusted by cell culture liquid obtained from a cell breeding culture tank provided independently of the biochemical treatment tanks and water or a part of hot water returning to a reduction well, hydrogen sulfide-containing gas is supplied thereinto and desulfurized thereat. With lowering of activation at the biochemical treatment tanks and with lowering of desulfurization ability there, the acidified reaction liquid is removed and is added to the hot water returning to the reduction well. Accordingly, addition of inorganic nutritive salt for cell breeding becomes unnecessary. A geothermal power plant desulfurization system is constructed so that cells are separated by use of a cell separation filter from the acidified reaction liquid removed from the biochemical treatment tanks and the cells so separated are returned to the biochemical treatment tanks.

1 Claim, 8 Drawing Sheets

GEOTHERMAL POWER PLANT DESULFURIZATION METHOD

BACKGROUND OF THE INVENTION:

1. Field of the Invention:

The present invention relates to a desulfurization method and a desulfurization system to remove sulfur from hydrogen sulfide-containing gas by use of cells at a geothermal power plant.

2. Description of the Prior Art:

The hydrogen sulfide-containing gas generated at a geothermal power plant has so far been desulfurized by a plant using ferric sulfate. In said desulfurization plant, ferrous sulfate and sulfur are generated. Ferrous sulfate after the sulfur is separated therefrom is oxidized to ferric sulfate using biochemical treatment equipment with air being blown thereinto and is returned to the desulfurization plant.

In said desulfurization method, there are such problems that, microorganisms being used indirectly therefor, the system becomes complicated and the microorganisms used in the biochemical treatment equipment being iron-oxidizing bacteria to react at a normal temperature, the reaction velocity is slow and the plant becomes enormously large, etc.

In order to solve these problems, the inventors of the present invention have found, and filed a patent application (Japanese Pat. Appl. 93-84237) for, a method in which hydrogen sulfide-containing gas generated at a geothermal power plant is directly led to, and desulfurized in, a biochemical treatment tank using high temperature acidophilic sulfur-oxidizing bacteria, and culture liquid of the biochemical treatment tank acidified by sulfuric acid generated by desulfurization is added to hot water returning to a reduction well. With this method, an effective desulfurization treatment can be carried out and yet a blockade of the reduction well due to the pH value of the hot water returning to the reduction well becoming higher can be avoided.

A desulfurization method at a geothermal power plant according to said method is outlined below with reference to FIG. 9. In FIG. 9, hot water 201 taken out from a production well 1 is separated into steam 4 and hot water 202 by use of a flasher 3. The steam 4, being led to a steam turbine 5 for power generation and being condensed at a condenser 6 after used for power generation, is returned to a reduction well 7 together with the hot water 202. High density hydrogen sulfide-containing gas 8 which is not condensed at the condenser 6 is oxidized at a biochemical treatment tank 10 to low density hydrogen sulfide-containing gas 11 and is dispersed into the air.

The pH value of culture liquid of the biochemical treatment tank 10 is lowered with time together with the hydrogen sulfide being converted to sulfuric acid. Accompanying the sulfuric acid generation, the acidified culture liquid 48 is taken out from the biochemical treatment tank 10 and is injected into the reduction well 7 together with the hot water 202. The pH value of the hot water 202 being lowered thereby, a fear of a blockade of the reduction well 7 due to scale sticking is mitigated. On the other hand, new culture liquid 50, of the same amount as the acidified culture liquid 48 so taken out, is led into the biochemical treatment tank 10 from a culture liquid tank 49 and desulfurization is done continuously.

In said geothermal power plant desulfurization method, due to lowering of pH value of the culture liquid or due to increase of salt density by adding alkali for neutralization thereof, lowering of desulfurization rate at the biochemical treatment tank occurs with time, and for avoidance thereof, a large amount of culture liquid for exchange is required, thus inorganic nutritive salt to be used for culture liquid results in a high cost.

SUMMARY OF THE INVENTION:

In view of the technological level, it is an object of the present invention to provide a geothermal power plant desulfurization method which has no such shortcomings as in the conventional geothermal power plant desulfurization method making use of hydrogen sulfide-containing gas treatment technology by use of microorganisms.

It is also an object of the present invention to provide a geothermal power plant desulfurization system by which a continuous and economical gas desulfurization can be done without using two biochemical treatment tanks to be switched one after the other.

According to the present invention, there is disclosed a geothermal power plant desulfurization method in which hot water taken out from a production well is separated into steam and hot water, the steam so obtained, after used for power generation, is condensed and separated into condensed water and hydrogen sulfide-containing gas, the hydrogen sulfide-containing gas is desulfurized at a biochemical treatment tank using high temperature acidophilic sulfur-oxidizing bacteria with the hydrogen sulfide being oxidized and converted to sulfuric acid, and reaction liquid acidified by the sulfuric acid so generated is added to the hot water returning to a reduction well. In order to attain said object, the initial cell density of the reaction liquid of the biochemical treatment tank is adjusted by cell culture liquid obtained from a cell breeding culture tank provided independently of said biochemical treatment tank and water or a part of the hot water returning to the reduction well, the hydrogen sulfide-containing gas is supplied into, and desulfurized at, the biochemical treatment tank, and with lowering of activation at the biochemical treatment tank and with lowering of desulfurization ability there, the acidified reaction liquid being taken out and new reaction liquid being prepared by use of cells bred at said cell breeding culture tank, thus desulfurization is continued and the reaction liquid so taken out is injected into the hot water returning to the reduction well.

According to the present invention as mentioned above, sulfur-oxidizing bacteria are bred at a cell breeding culture tank provided independently of a biochemical treatment tank and only the desulfurization reaction is done at the biochemical treatment tank. Thus, there is no need to adding inorganic nutritive salt for cell breeding at the biochemical treatment tank, and water like city water or hot water returning to a reduction well (hot water after separation of steam of hot water taken out from a production well and condensed water of steam used for power generation) can be used. If water is used, it is to be heated where necessary.

As for sulfur-oxidizing bacteria used in the present invention, Sulfolobus acidocaldarius, Sulfolobus solfataricus, Sulfolobus mirabilis, Desulforolobus ambivalens, Acidianus infernus, Acidianus brierleyi, etc. are named. These bacteria oxidize hydrogen sulfide to $SO_4^{2-}$, $S_2O_4^{2-}$ via sulfur.

As a preferred embodiment according to the present invention, two biochemical treatment tanks are provided in parallel, desulfurization is done first at one of the biochemical treatment tanks, and with lowering of pH value of reaction liquid due to sulfuric acid generated accompanying with desulfurization reaction and with lowering of desulfurization ability (activation of the biochemical treatment tank), the biochemical treatment tank is switched to the other. All the amount of the reaction liquid acidified in the biochemical treatment tank of which desulfurization ability lowered is taken out and is added to hot water returning to a reduction well. New cells bred at a cell breeding culture tank and water or hot water returning to the reduction well are supplied into the biochemical treatment tank after the acidified reaction liquid is taken out therefrom, and the reaction liquid is thus prepared. The biochemical treatment tank is not limited to two units but three or more units are also considered.

Judgement of the timing of switching of the biochemical treatment tanks is done by measuring activation of the biochemical treatment tank by use of an activation monitoring device. Various types of activation monitoring devices can be used. For example, a hydrogen sulfide density measuring device provided in the vicinity of an outlet of low density hydrogen sulfide-containing gas of the biochemical treatment tank, a turbidity measuring meter to measure turbidity of the reaction liquid, a pH measuring device of the reaction liquid, etc., can be used.

Treatment conditions at the biochemical treatment tank differ by the kinds of cells used. In the case of use of said sulfur-oxidizing bacteria, a range of temperatures of 70°–95° C. and of pH values of 1–3 is preferable, and if the initial cell density of sulfur-oxidizing bacteria at the biochemical treatment tank is set at $4 \times 10^7$ cells/ml or more, then a good desulfurization rate can be obtained.

Further, according to the present invention, it is also disclosed that a desulfurization system is constructed, as mentioned below, so as to solve the shortcomings of a geothermal power plant desulfurization system which is so constructed that a biochemical treatment tank using high temperature acidophilic sulfur-oxidizing microorganisms and a cell breeding culture tank independent of said biochemical treatment tank is being provided, hydrogen sulfide is desulfurized at said biochemical treatment tank, and acid water containing sulfuric acid generated thereby is injected into a reduction well so as to avoid a blockade of the reduction well.

That is, in a geothermal power plant desulfurization system according to the present invention, a construction is so made that a cell separation filter is provided in a biochemical treatment tank, acid water and microorganisms are taken out by means of the cell separation filter from culture liquid acidified in the biochemical treatment tank, and the microorganisms are returned to the biochemical treatment tank.

By employing such construction to provide a cell separation filter in a biochemical treatment tank, the cells filtrated by the cell separation filter can be returned to the biochemical treatment tank, concurrently with acid water, i.e. sulfuric acid being taken out from the biochemical treatment tank. Accordingly, a continuous desulfurization treatment becomes possible with such construction without using two treatment tanks to be switched one after the other.

A cell separation filter employed in the present invention can be made from either of ceramics material or polysulfone material, both having an endurance ability against temperature, acidity and alkalinity.

Further, in a desulfurization system according to the present invention, a back wash line having an alkali injection unit is preferably provided on a cell separation filter. By providing such back wash line, the cell separation filter, when clogged, is infected therefrom with alkali, sodium hydroxide for example, then the compressed dense microorganisms become cell lysis and a filtratable condition can be restored.

Further, in a geothermal power plant desulfurization system according to the present invention, such construction is preferably employed as that hot water exhausted from a geothermal power plant is used as heat source to keep the temperature of a biochemical treatment tank constant. As an example for this purpose, heat exchangers with hot water are provided in a biochemical treatment tank, a culture liquid tank and a cell breeding culture tank, thereby the temperature of the biochemical treatment tank can be kept constant without heating from outside.

Further, in a desulfurization system according to the present invention, such construction is preferably employed as that the hot water before it is used as said heat source is added to with acid water generated at a biochemical treatment tank. By use of such construction, hot water before it is led to heat exchangers is added to acid water, the pH value thereof is lowered and an incident to cause a blockade of a reduction well due to scale sticking mainly consisting of silica can be avoided.

Further, in a desulfurization system according to the present invention, condensed water exhausted from a geothermal power plant is preferably led to a culture liquid tank or to a cell breeding culture tank as a water source for microorganism culture. By use of such construction, culture liquid can be self-supplied within the geothermal power plant.

Further, in a desulfurization system according to the present invention, an air pump to supply air to a biochemical treatment tank or an oxygen supply device having an oxygen production device and an oxygen supply pump to supply oxygen to a biochemical treatment tank is preferably provided. As for an oxygen production device, an air separation device by use of a pressure swing adsorption method can be employed (PSA type oxygen production device to produce $O_2$ by repeat of air being compressed, $N_2$ gas contained therein being selectively adsorbed by adsorbent and $N_2$ gas being separated by decompression). In this case, oxygen is preferably so supplied as to set the mole ratio of hydrogen sulfide and oxygen (oxygen/hydrogen sulfide) at 80 or more out of the gas components supplied into the biochemical treatment tank.

By employing such construction as to supply air or oxygen into the biochemical treatment tank, enough oxygen is supplied for hydrogen sulfide being oxidized and converted to sulfuric acid at the biochemical treatment tank, no sulfur precipitation as an intermediate product is formed and a larger amount of sulfuric acid generation is obtained for a hydrogen sulfide load, and there is no fear of a filter blockade caused by sulfur precipitation.

DESCRIPTION OF THE PREFERRED EMBODIMENTS:

Now, the present invention will be described below in greater detail in connection with the preferred embodiments.
(A first preferred embodiment)

Figure 1:
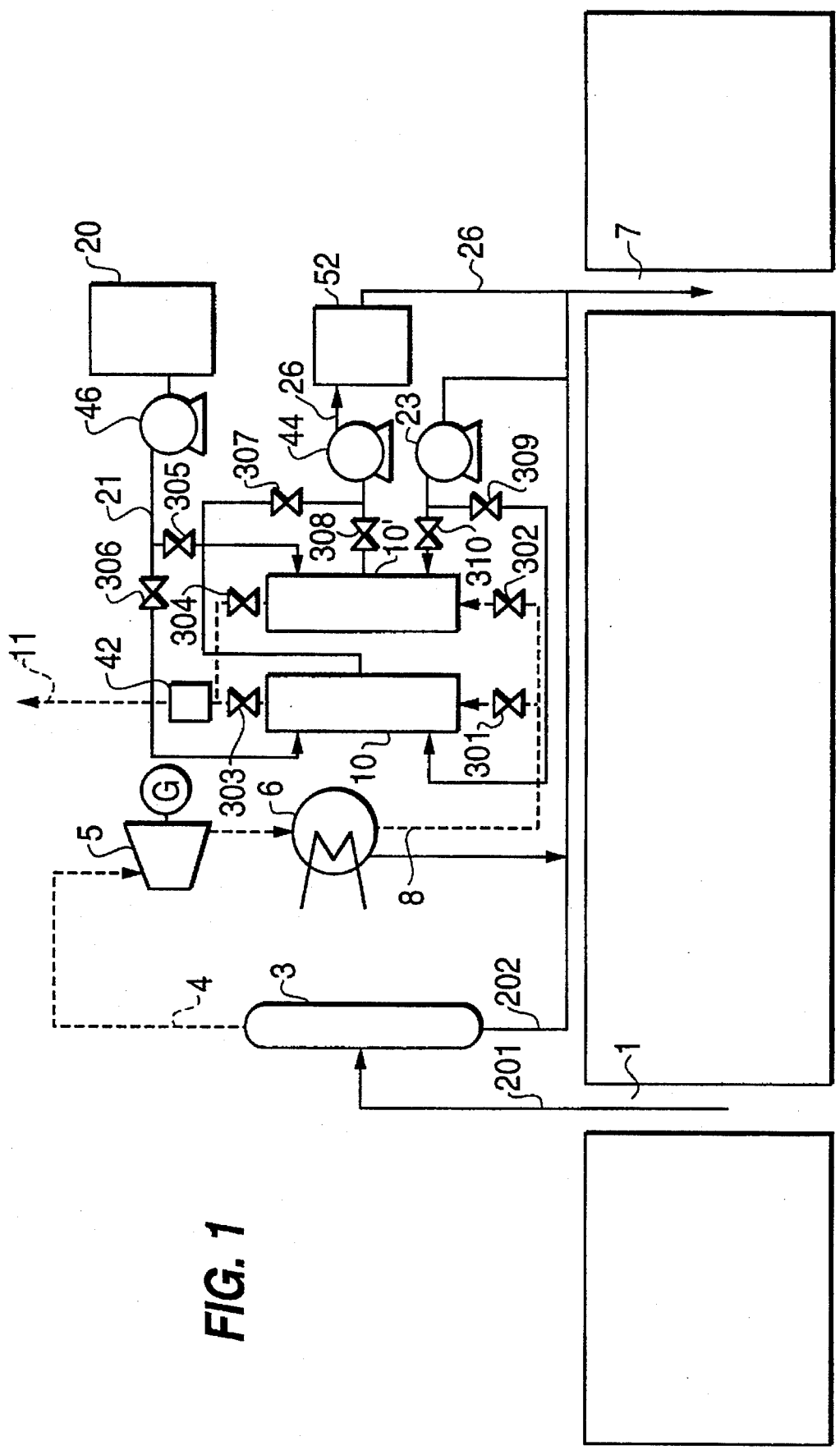
FIG. 1 is a flow diagram showing a first preferred embodiment of a geothermal power plant desulfurization method according to the present invention.

FIG. 1 is a flow diagram showing one example of a geothermal power plant desulfurization method according to the present invention. In the flow diagram of FIG. 1, hot water 201 taken out from a production well 1 is separated into steam 4 and hot water 202 by use of a flusher 3. The steam 4 is introduced into a steam turbine 5 and is used for power generation. The steam 4 used for power generation is condensed at a condenser 6 and returned to a reduction well 7 together with hot water 202. High density hydrogen sulfide-containing gas 8 not condensed at the condenser 6 is introduced into a biochemical treatment tank 10 in a state of valves 301 and 303 being opened and valves 302 and 304 being closed and is removed of its hydrogen sulfide by oxidation to low density hydrogen sulfide-containing gas 11 and is dispersed into the air. Accompanying the conversion of hydrogen sulfide to sulfuric acid at the biochemical treatment tank 10, the pH value thereof is lowered with time, and with the pH value becoming 1 or less, the desulfurization rate is lowered. With the desulfurization rate at the biochemical treatment tank 10 being lowered and with the density of hydrogen sulfide measured by a hydrogen sulfide monitoring device (a density measuring device using gas diffusion barrier type sensor obtainable on the market) provided at a gas outlet of the biochemical treatment tank 10 becoming 10 ppm or more, then valves 301 and 303 are switched to closed and valves 302 and 304 to "open" and high density hydrogen sulfide-containing gas is introduced into the biochemical treatment tank 10' and desulfurized. Switching of the biochemical treatment tanks is to be done at the time of the transmission rate becoming 60% or less if a turbidity meter for measuring turbidity of reaction liquid is used as an activation monitoring device of the biochemical treatment tank, or at the time of the pH value becoming 1 or less if a pH meter using a glass electrode is used.

On the other hand, a valve 307 is opened and reaction liquid acidified at the biochemical treatment tank 10 is taken out by a reaction liquid suction pump 44 and reserved at an acid water reservoir 52. Then, the valve 307 being closed and a valve 309 being opened, hot water is supplied into the biochemical treatment tank 10 by a hot water supply pump 23. Thereafter, the valve 309 being closed and a valve 306 being opened, cells 21 are injected by a cell supply pump 46 into the biochemical treatment tank 10 from a cell breeding culture tank 20 so as to maintain appropriate cell density. As an appropriate cell density, the initial cell density is set at around $4 \times 10^7$ cells/ml in case of said sulfur-oxidizing bacteria being used and then a high desulfurization rate can be obtained.

A cell breeding culture tank 20 is, for example, a culture tank of an aeration mixing type, and into this cell breeding culture tank 20, geothermal water or water which contains fermentation residue of starch or alcohol production or fermentation liquid of cereals by 0.1% or more as a nutriment organic matter for culture liquid and is adjusted to pH 2 with mixture of acidified reaction liquid of the biochemical treatment tank is injected, and sulfuroxidizing bacteria are bred with the temperature being kept at around 70° C. by an appropriate heat exchange means.

Thereafter, with lowering of desulfurization rate at the biochemical treatment tank 10', the valves 302 and 304 being closed and the valves 301 and 303 being opened, high density hydrogen sulfide-containing gas 8 is introduced into the biochemical treatment tank and desulfurization is continued. With repetition of these operations, high density hydrogen sulfide-containing gas 8 is desulfurized and acidified reaction liquid 26 is generated, continuously. A part of the generated acid reaction liquid 26 is injected into a reduction well 7 together with the hot water returning to the reduction well 7 (hot water 202 and condensed water from a steam turbine), the pH value of the hot water is lowered to 5 or less and fear of a blockage of the reduction well 7 due to scale sticking is mitigated. At this stage, a flow ratio of the hot water and the acid reaction liquid (pH≈1) returning to the reduction well 7 is approximately 1000–10000:1 and the temperature is around 90° C.

(Experiment example 1)

Figure 2:
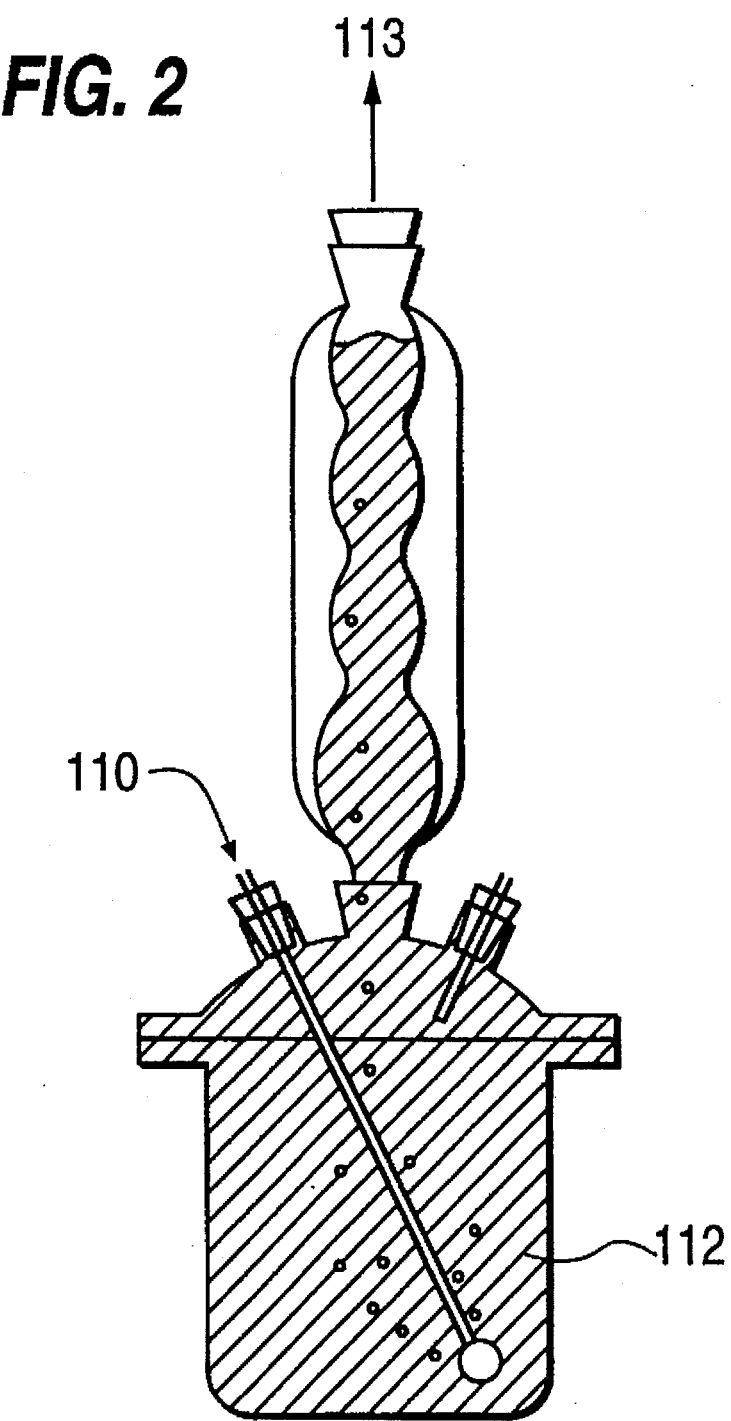
FIG. 2 is a schematic sectional view of a device used for Experiment examples 1 and 2.
Figure 3:
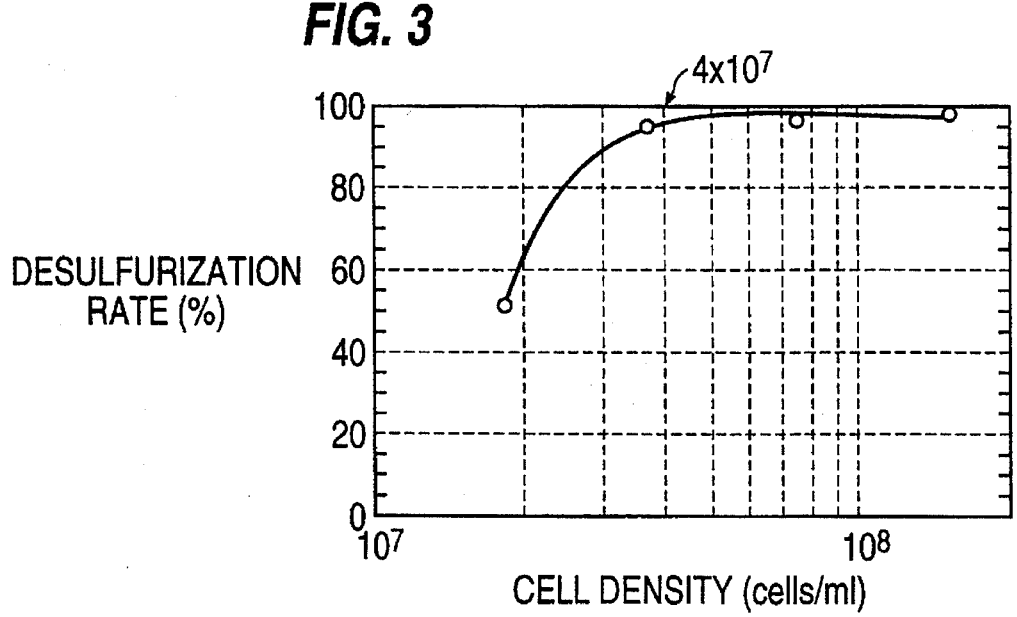
FIG. 3 is a graph showing correlation between cell density and desulfurization rate in the reaction liquid at Experiment example 1.

By use of a device shown in FIG. 2, experiments on desulfurization of hydrogen sulfide-containing gas were carried out. Within a reaction device 112 containing 1.2 liters of reaction liquid at the temperature of 70° C. and of the pH 2.5 with the components of Table 1 as well as Sulfolobus acidocaldarius strain 7 as one of high temperature acidohilic microorganism, hydrogen sulfide-containing gas 110 (2000 ppm $H_2S$, 25% $CO_2$, 25% $O_2$, base $N_2$) at normal room temperature (25° C.) was blown with the flow velocity of 24 l/h. For reference, in FIG. 2, numeral 113 designates refined gas. Correlation between cell density of reaction liquid and desulfurization rate is shown in FIG. 3. Here, desulfurization rate (%) equals (inlet hydrogen sulfide density-outlet hydrogen sulfide density) x 100/(inlet hydrogen sulfide density). From FIG. 3, it is found that a high desulfurization rate of 90% or more can be obtained at a cell density of $4 \times 10^7$ cells/ml or more.

TABLE 1

| Components | Amount (g/l) |
| --- | --- |
| $(NH_4)_2SO_4$ | 0.4 |
| KCl | 0.2 |
| $K_2HPO_4$ | 0.2 |
| $MgSO_4 \cdot 7H_2O$ | 0.4 |
| $Na_2MoO_4$ | $3 \times 10^{-4}$ |
| yeast extract | 0.2 |

(Experiment example 2)

Figure 4:
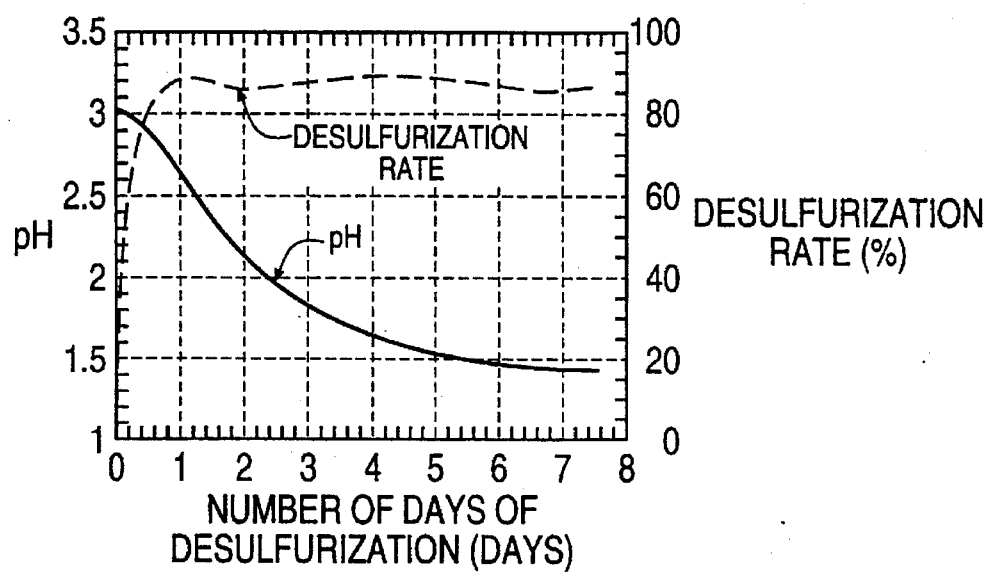
FIG. 4 is a graph showing changes by time of pH value and desulfurization rate at Experiment example 2.

By use of a device shown in FIG. 2, experiments on desulfurization of hydrogen sulfide-containing gas were carried out. Within a reaction device 112 containing 1.2 liters of reaction liquid (city water) at the temperature of 70° C. and of the pH value being adjusted to 2.5 not containing inorganic nutritive salt, Sulfolobus acido-caldarius strain 7, same as used in Experiment example 1, was put in together with the breeding culture liquid of the components of Table 2 (approximately 1/25 of the reaction liquid volume) so as to set the cell density in the reaction liquid at $4 \times 10^7$ cells/ml, and hydrogen sulfide-containing gas 110 (2000 ppm $H_2S$, 25% $CO_2$, 25% $O_2$, base $N_2$) at normal room temperature (25° C.) was blown with the flow velocity of 24 l/h. Changes by time of pH value and desulfurization rate at that time are shown in FIG. 4. From FIG. 4, it is found that a high desulfurization rate of 90% or more can be maintained for more than. one week even if city water not containing nutritive salt is used as the reaction liquid.

TABLE 2

| Components | Amount (g/l) |
| --- | --- |
| $(NH_4)_2SO_4$ | 1.3 |
| NaCl | 0.2 |
| $KH_2PO_4$ | 0.3 |
| $MgSO_4.7H_2O$ | 0.25 |
| $CaCl_2/2H_2O$ | 0.05 |
| yeast extract | 1.0 |
| glucose | 1.0 |
| casamino acids | 1.0 |

According to a geothermal power plant desulfurization method of the present invention, sulfur oxidation cells are bred at a cell breeding culture tank provided independently of a biochemical treatment tank and only the desulfurization reaction is done at the biochemical treatment tank. Thereby, at the biochemical treatment tank, such water as city water or hot water returning to a reduction well (hot water after separated of steam of hot water taken out from a production well and condensed water of steam after used for power generation) can be used as additional liquid for preparation or pH adjustment of the reaction liquid, and the addition of inorganic nutritive salt for cell breeding as so far been required at the biochemical treatment tank becomes unnecessary. Thus, the amount of inorganic nutritive salt used as a whole can be decreased nearly to 1/10. Since a large amount of reaction liquid for exchange is required at the biochemical treatment tank, the effect of cost reduction by a fact that such water as hot water or city water can be used in place of the culture liquid as so far required is sizable.

Figure 5:
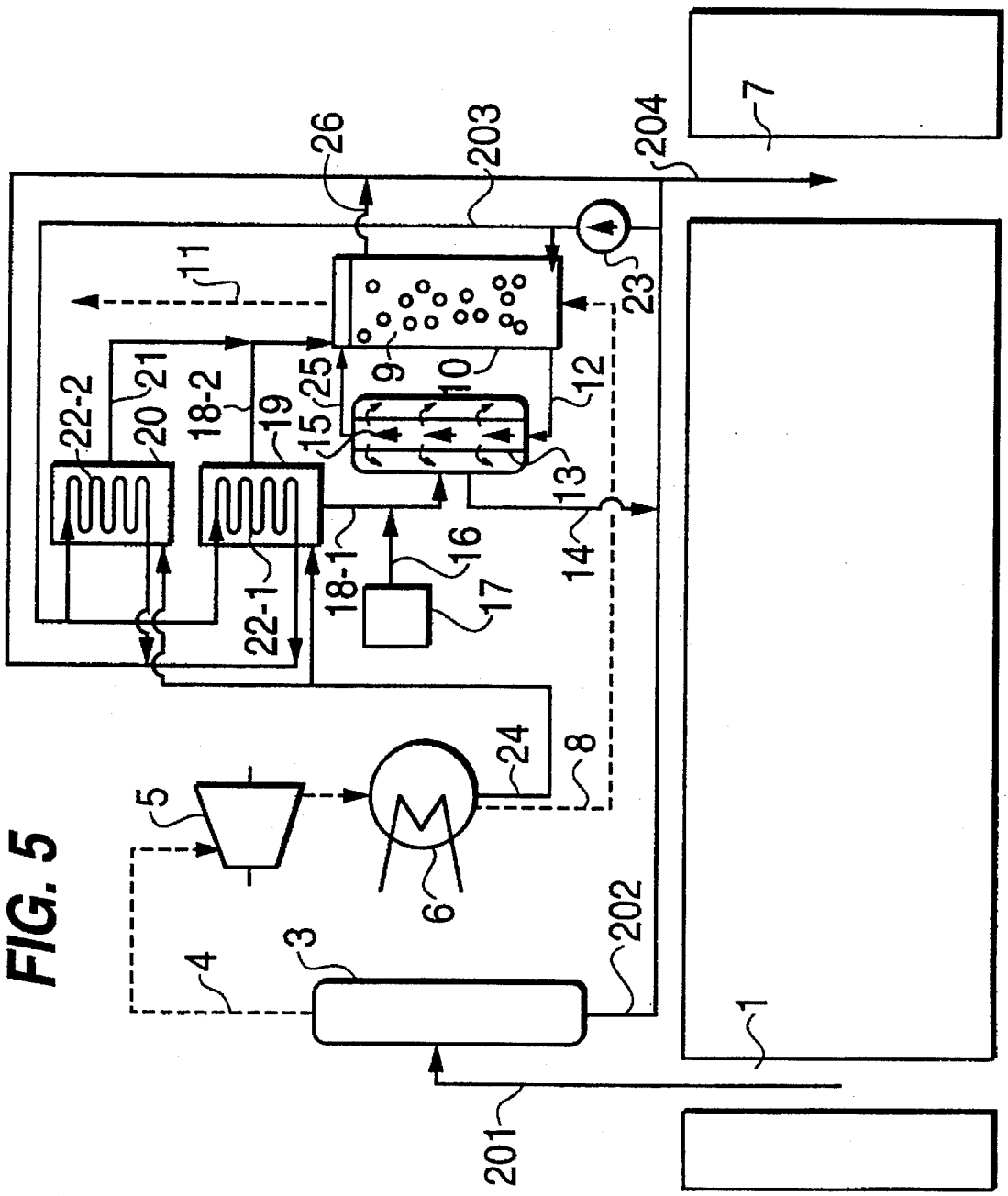
FIG. 5 is a flow diagram showing a second preferred embodiment of a geothermal power plant desulfurization system according to the present invention.
Figure 6:
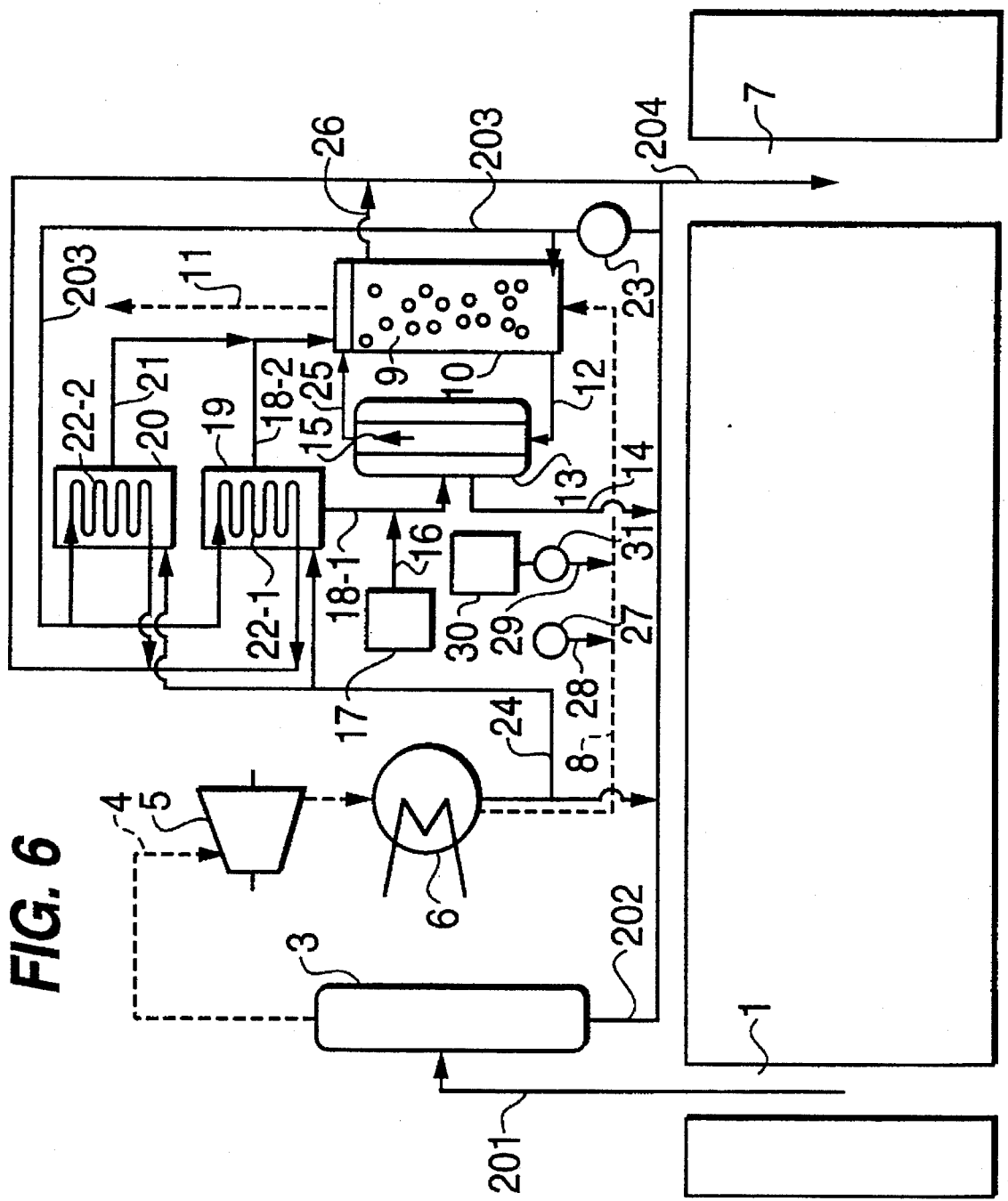
FIG. 6 is a flow diagram showing a third preferred embodiment of a geothermal power plant desulfurization system according to the present invention.

Next, a geothermal power plant desulfurization system according to the present invention is described more in detail based on preferred embodiments shown in FIG. 5 and FIG. 6.

(A second preferred embodiment)

Description is made of a second preferred embodiment shown in FIG. 5. As shown in FIG. 5, hot water 201 (150° C.) taken out from a production well 1 is separated into steam 4 and hot water 202 by use of a flusher 3. The steam 4 (130° C.) is introduced into a steam turbine 5 and is used for power generation. The steam 4 used for power generation is condensed at a condenser 6 and separated into condensed water 24 and non-condensed gas 8.

High density hydrogen sulfide-containing gas 8 not condensed at the condenser 6 (contained by 0.5 wt. % in the steam at a turbine inlet, non-condensed gas components: $H_2S$ 5 wt. %, $CO_2$ 90%, other 5%) is oxidized at a biochemical treatment tank 10 of a bubbling tower type in which culture liquid 9 containing sulfur-oxidizing microorganism (temperature 70° C., pH 2.5: acid of sulfuric acid, cell density: $2\times10^{14}$ cells/ton) is filled, and low density hydrogen sulfide-containing gas 11 is generated and is dispersed into the air.

Condensed water 24 is sent to a culture liquid tank 19 and to a cell breeding culture tank 20 and is used as a water source for microorganism culture. As microorganism used in a biochemical treatment tank 10, one kind of Sulfolobus genus is used. The pH value of culture liquid 9 of the biochemical treatment tank 10 is lowered with time accompanying conversion of hydrogen sulfide to sulfuric acid. A part of the culture liquid 12 acidified together with generation of sulfuric acid is taken out from the biochemical treatment tank 10 via a cell separation filter 13 as acid water 14.

Construction of the cell separation filter 13 is preferably a cross flow type which has a vertical flow against the filtration surface, and material thereof is taken from acid resistant, alkali resistant and heat resistant ones made of ceramics or polysulfone.

When the acidified culture liquid 12 is introduced into the cell separation filter 13 from the biochemical treatment tank 10, a line velocity of 3 m/s or more in a vertical direction against filtration surface is maintained within the cell separation filter 13, and microorganisms 15 and acid water 14 are separated from the acidified culture liquid 12 at the filtration pressure of 0.1 atm.

At this time, back wash is made with pressure at the rate of 5 seconds per minute by new culture liquid 18-1 of 3 atm or less. Microorganisms 15 separated from filtration surface by back wash are returned to the biochemical treatment tank 10 from a line 25 together with other acidified culture liquid. In case the back wash pressure becomes 5 atm or more, sodium oxide liquid of 6N is injected from an alkali liquid tank 17 via an alkali injection line 16 provided in the back wash line and the compressed dense microorganisms on the filter surface become immediately cell lysis by alkali, and filtration and back wash become possible again.

Acid water 14 so obtained and a part of the liquid acidified at the biochemical treatment tank 10 being injected into a reduction well 7 via a line 26 together with hot water 204, the pH value of hot water 202 is lowered from about 8 to 5.5 at the temperature of about 90° C. and a blockade of reduction well 7 mainly due to scale sticking of silica is mitigated. On the other hand, new culture liquid 18-2 of the same amount as the acid water 14 so taken out is introduced into the biochemical treatment tank 10 from a culture liquid tank 19 together with cells 21 bred at a cell breeding culture tank 20 and desulfurization is carried out continuously.

The Sulfolobus genus is breedable at a high temperature and under an acid condition and is also breedable by subordinate nutrition. In the independent nutrition where breeding is usually made with sulfur being oxidized, a breeding velocity is generally small. So, by the Sulfolobus genus being used, it becomes possible that at the time of breeding, a large amount of culture is made by the subordinate nutrition and at the time of desulfurization, hydrogen sulfide is oxidized to sulfuric acid by independent nutrition. The amount of cells in the biochemical treatment tank 10 is kept more than a specified level by the recovery by means of the filter 13 and by the injection from the cell breeding culture tank 20.

While desulfurization and sulfuric acid generation are made, hot water 203 of the lowered pH value of 5.5 is introduced by a pump 23 into the biochemical treatment tank 10 and into heat exchangers 22-1 and 22-2 provided at the culture liquid tank 19 and the cell breeding culture tank 20, respectively, and the temperature in each tank is maintained at 70° C. by the heat exchanged between the culture liquid and the hot water 203. Usually, if the pH value of hot water decreases to about 5.5 or less, no silica scale is formed. As the pH value of hot water 203 is being lowered to 5.5 as mentioned above, a blockade of the reduction well 7 mainly due to sticking of silica scale does not occur even if the temperature of hot water is lowered by the heat exchange.

(A third preferred-embodiment)

Next, a third preferred embodiment shown in FIG. 6 is described. In FIG. 6, numeral 27 designates an air pump, numeral 30 is, for example, a PSA type oxygen production device and numeral 31 is an oxygen supply pump. Air pump 27 and oxygen supply pump 31 are so constructed as to introduce air or oxygen into the high density hydrogen sulfide-containing gas 8 and supply it to the biochemical treatment tank 10. Other constructions are the same as the second preferred embodiment shown in FIG. 5.

In said system of the third preferred embodiment, air 28 is supplied by the air pump 27 and oxygen 29 is supplied by the oxygen production device 30 for mixture into the high density hydrogen sulfide-containing gas 8 so as to set the mole ratio of hydrogen sulfide and oxygen (oxygen/hydrogen sulfide) at 80 or more, out of the gas components of the high density hydrogen sulfide-containing gas 8 introduced into the biochemical treatment tank 10.

Thus, as a function and effect of a necessary amount of air or oxygen being supplied into the biochemical treatment tank 10, the high density hydrogen sulfide-containing gas 8 is completely oxidized of its hydrogen sulfide at the biochemical treatment tank 10 and is dispersed into the air as the low density hydrogen sulfide-containing gas 11.

(Experiment example 3)

Figure 7:
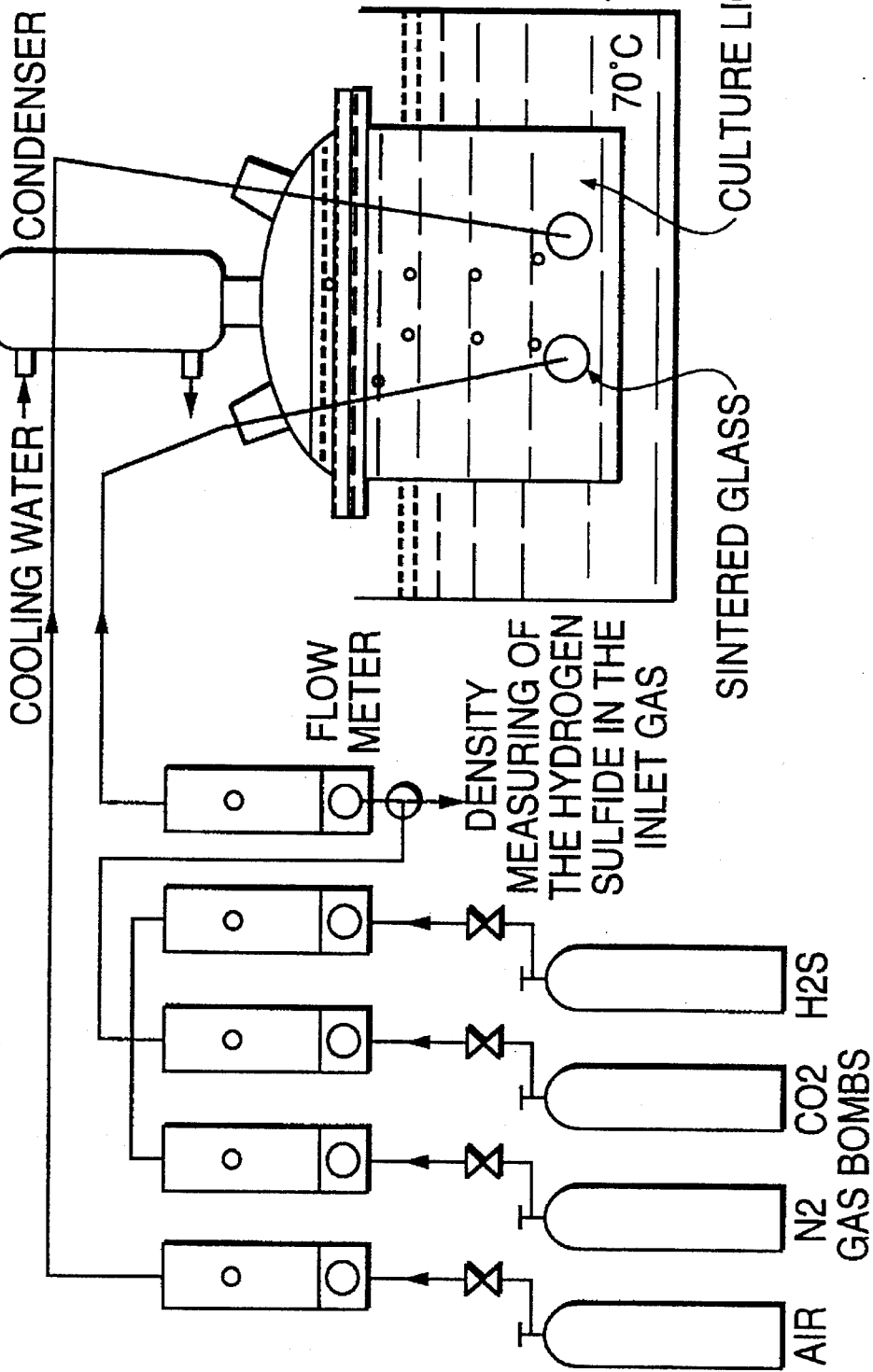
FIG. 7 is a flow diagram showing an experimental device of a geothermal power plant desulfurization system according to the present invention.

Tests on a table were carried out on the influence of mole ratio of hydrogen sulfide and oxygen (oxygen/hydrogen sulfide) given on sulfuric acid conversion rate (sulfuric acid generation amount/desulfurization amount). A flow diagram of the test device is shown in FIG. 7, culture liquid components are shown in Table 3 and gas components are shown in Table 4.

TABLE 3

| Reagent/culture medium | Amount (g/l) |
| --- | --- |
| $(NH_4)_2SO_4$ | 0.4 |
| KCl | 0.2 |
| $K_2HPO_4$ | 0.2 |
| $MgSO_4.7H_2O$ | 0.4 |
| $Na_2MoO_4$ | 0.0003 |
| $FeSO_4.7H_2O$ | 0.5 |
| yeast extract | 0.2 |

Diluted by distilled water, culture liquid being pH 2.5 (adjusted by sulfuric acid)

TABLE 4

| No. | $H_2S$ | $CO_2$ | $O_2$ | $O_2/H_2S$ |
| --- | --- | --- | --- | --- |
| 1 | 0.36 | 75 | 5 | 14 |
| 2 | 0.25 | 75 | 10 | 40 |
| 3 | 0.25 | 75 | 20 | 80 |

Unit: v/v %
Other components than the above being all nitrogen.

In the tests, culture liquid in which Sulfolobus being high temperature acidophilic sulfur-oxidizing bacteria is contained in the density of $1 \times 10^8$ cells/ml and the temperature of which is maintained at 70° C. is filled in a flask of inner volume of around 1.2 l and height of around 130 mm, a mixture gas adjusted of its hydrogen sulfide density, oxygen density and $CO_2$ density is blown into the flask from its bottom part via a sintered glass filter with the flow amount of 24 liter/h for making a contact oxidation with the culture liquid, and the hydrogen sulfide density in the gas was measured.

Using the results of experiments, desulfurization amount, that is, [(inlet hydrogen sulfide density—outlet hydrogen sulfide density) x mixture gas flow amount x time] was calculated. Further, sulfuric acid density in the culture liquid was measured by ion chromatography and sulfuric acid generation amount was obtained. From desulfurization amount and sulfuric acid density, sulfuric acid conversion rate was calculated (sulfuric acid conversion rate=sulfuric acid density x culture liquid amount/desulfurization amount x 100).

Figure 8:
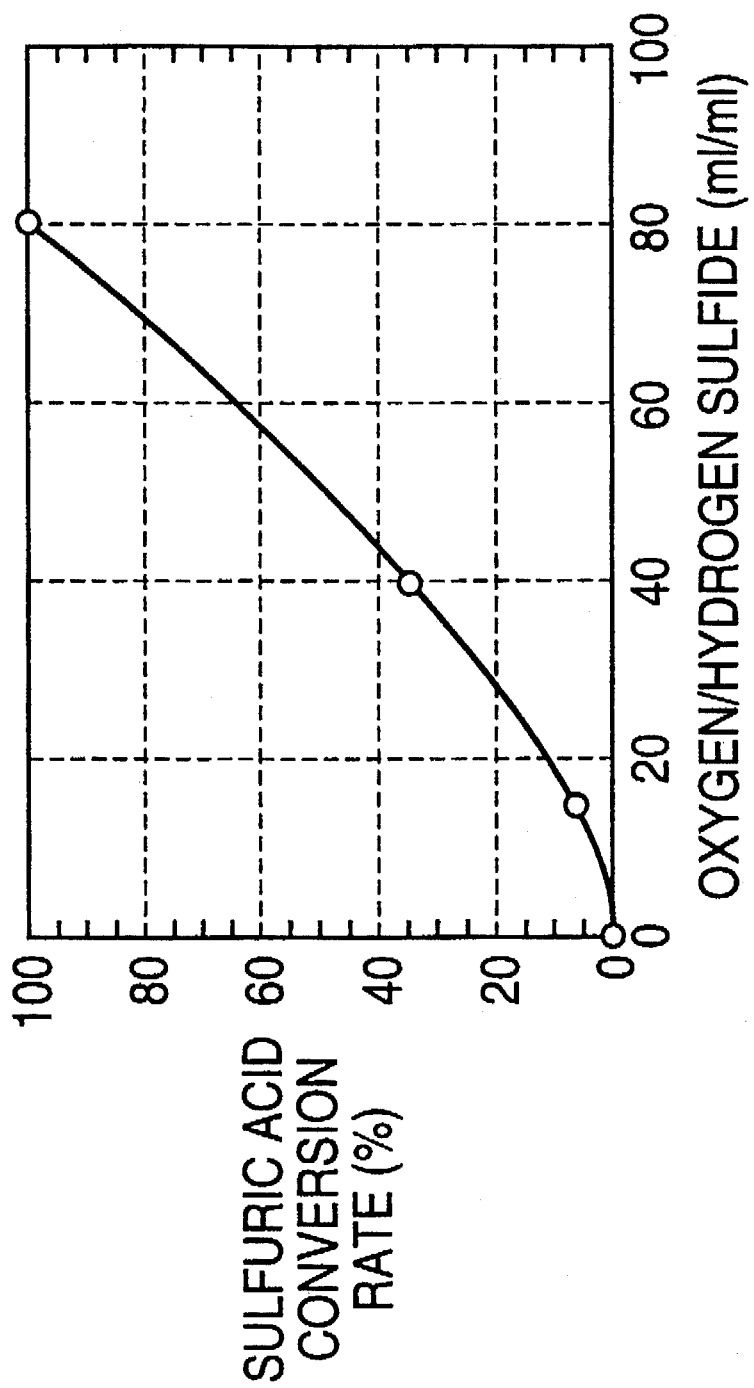
FIG. 8 is a graph showing a results of a test using the experimental device of FIG. 7.
Figure 9:
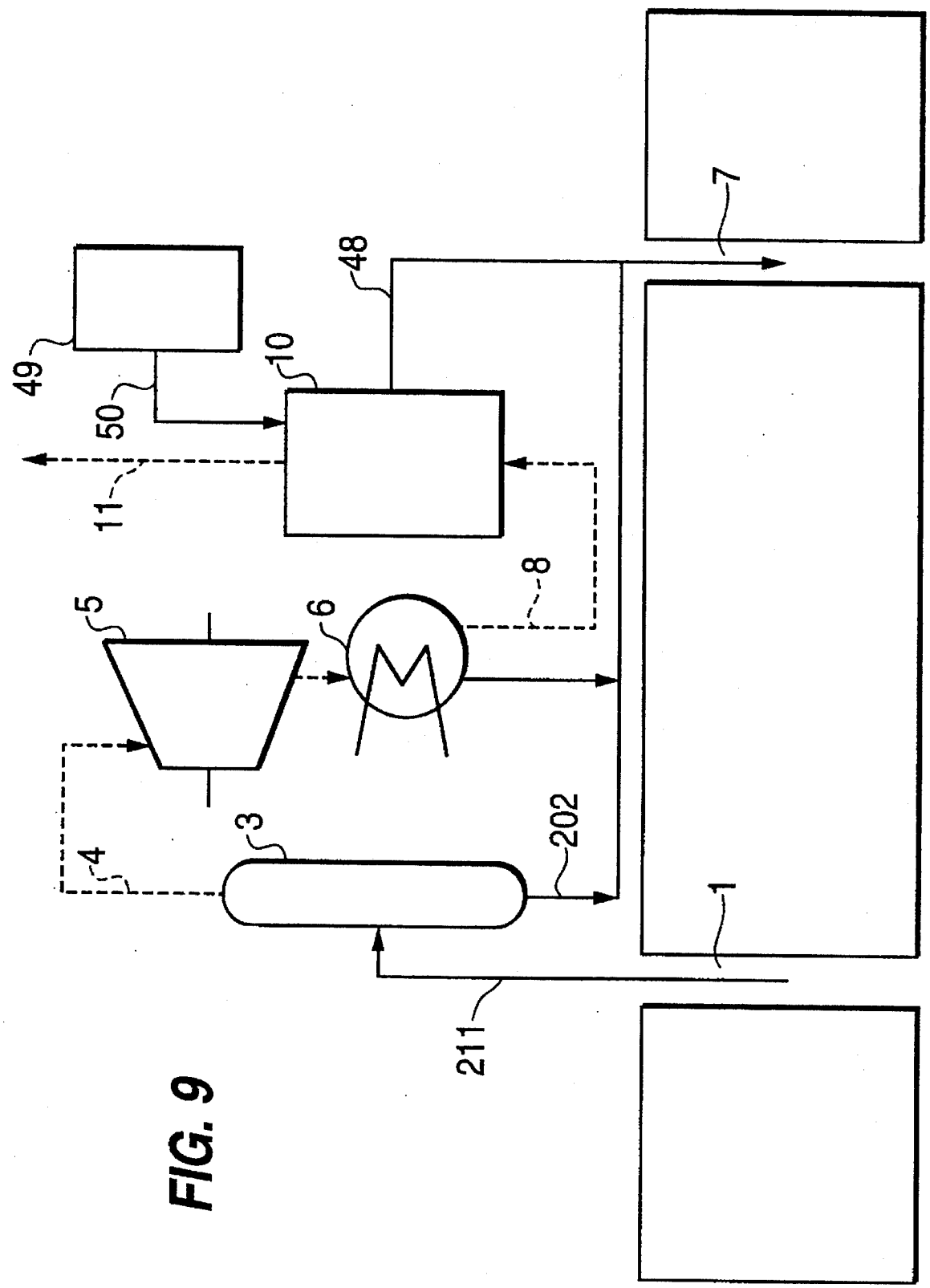
FIG. 9 is a flow diagram showing a geothermal power generation method according to the Japanese patent application 93-84237.

The results are shown in FIG. 8. The larger is the ratio of oxygen/hydrogen sulfide, the larger becomes the sulfuric acid conversion rate, and when the oxygen/hydrogen sulfide is 80 or more, the sulfuric acid conversion rate becomes almost 100%. From this, it is found that by the ratio of oxygen/hydrogen sulfide being maintained at 80 or more, 100% sulfuric acid conversion rate is maintained and precipitation of sulfur can be avoided.

Geothermal power plant desulfurization systems according to the present invention were described as above in concrete forms with reference to the preferred embodiments as shown in the figures. The present invention is, however, not to be limited to those preferred embodiments but various modifications to the concrete construction may be added within the range shown in the scope of claims of the present invention.

For example, in the first and second preferred embodiments, geothermal water coming out from the flusher 3 is injected into the heat exchanger 22-2 provided in the cell breeding culture tank 20, but the construction may be such that a heat exchanger is provided within the biochemical treatment tank 10 and that geothermal water is led thereinto.

In a geothermal power plant desulfurization system according to the present invention, cells bred in a cell breeding culture tank are injected continuously or intermittently into a biochemical treatment tank and cells filtrated by a cell separation filter are returned to the biochemical treatment tank. Thus, the cell amount in the biochemical treatment tank is maintained at more than a certain specified level, and continuous desulfurization and pH adjustment of hot water becomes possible without causing decrease of the desulfurization rate even if two biochemical treatment tanks are not used alternately.

Further, by a back wash line having an alkali injection device being provided, if a filter is clogged by compressed dense cells, alkali is injected into the back wash line and cells are released, thereby clogs of the filter can be dissolved. If a filter is of a material that is acid resistant, alkali resistant and heat resistant, then deterioration of the filter is mitigated and by a self-supply of culture liquid within a plant, the cost of water introduced from outside can be saved.

If the construction is such geothermal water is introduced by a pump into a heat exchanger provided on a biochemical treatment tank, etc., the temperature of the biochemical treatment tank is kept constant by the heat of geothermal water being exchanged there. If sulfuric acid generated at the biochemical treatment tank is added to the hot water before heat exchange thereof is made, the pH value of the hot water introduced to the heat exchanger is lowered and a scale precipitation caused by lowering of the hot water temperature can be avoided.

Further, air from an air supply pump or oxygen from an oxygen supply device is supplied into the biochemical treatment tank, hydrogen sulfide is completely converted to sulfuric acid, velocity of sulfuric acid generation becomes higher and at the same time a blockade of the filter due to sulfur can be suppressed.

What is claimed is:

1. A geothermal power plant desulfurization method comprising:

separating hot water removed from a production well into steam and hot water;

condensing and separating the steam so obtained, after it has been used for power generation, into condensed water and hydrogen sulfide-containing gas;

desulfurizing the hydrogen sulfide-containing gas at a biochemical treatment tank using high temperature acidophilic sulfur-oxidizing bacteria with the hydrogen sulfide being oxidized and converted to sulfuric acid;

adding reaction liquid acidified by the sulfuric acid so generated to the hot water returning to a reduction well;

adjusting the initial cell density of the reaction liquid of the biochemical treatment tank by cell culture liquid obtained from a cell breeding culture tank provided independently of said biochemical treatment tank and water or a part of the hot water returning to the reduction well;

supplying the hydrogen sulfide-containing gas into, and desulfurizing the hydrogen sulfide-containing gas at, the biochemical treatment tank; and with lowering of activation at the biochemical treatment tank and with lowering of desulfurization ability there, removing the acidified reaction liquid and preparing new reaction liquid by use of cells bred at said cell breeding culture tank, thereby continuing desulfurization and injecting the reaction liquid so removed into the hot water returning to the reduction well.

* * * * *